United States Patent
Amari et al.

(10) Patent No.: US 8,637,056 B2
(45) Date of Patent: Jan. 28, 2014

(54) MIXTURE OF FATTY ACID ESTERS OF NATURAL ORIGIN AND ITS USE IN COSMETIC PREPARATIONS BASED ON OLIVE OIL DERIVATIVES

(75) Inventors: Sergio Amari, Paderno d'Adda (IT); Edoardo Pallucca, Settimo Milanese (IT)

(73) Assignee: Hallstar Italia S.R.L., Milan (IT)

( * ) Notice: Subject to any disclaimer, the term of this patent is extended or adjusted under 35 U.S.C. 154(b) by 190 days.

(21) Appl. No.: 13/125,393

(22) PCT Filed: Oct. 15, 2009

(86) PCT No.: PCT/IB2009/054542
§ 371 (c)(1),
(2), (4) Date: Apr. 21, 2011

(87) PCT Pub. No.: WO2010/046816
PCT Pub. Date: Apr. 29, 2010

(65) Prior Publication Data
US 2011/0201682 A1    Aug. 18, 2011

(30) Foreign Application Priority Data

Oct. 24, 2008 (IT) ................... MI08A1884

(51) Int. Cl.
*A61K 8/02* (2006.01)
*A61K 31/22* (2006.01)
*C07C 51/00* (2006.01)

(52) U.S. Cl.
USPC ........... 424/401; 514/549; 514/844; 554/124; 554/174; 554/115

(58) Field of Classification Search
None
See application file for complete search history.

(56) References Cited

U.S. PATENT DOCUMENTS 5,686,087 A    11/1997  Ansmann et al.
2006/0280709 A1*  12/2006  Ansmann et al. .......... 424/70.11
2008/0249172 A1   10/2008  Ansmann et al.

FOREIGN PATENT DOCUMENTS

DE        32 31 705 A1    3/1984
WO        2004082641 A1   9/2004

OTHER PUBLICATIONS

DE3231705, Use of branched-chain 2-ethylhexanoic esters as constituent of cosmetic compositions, 1984, Dragoco Gerberding Co. GMBH, English Translation, (5 pages).*
Boggia, R., et al., Chemical compositoin of olive oils of cultivar Colombia, 2005, Grassas y Aceites, vol. 56, issue 4, pp. 276-283.*
Akpan, E.J. et al., Fatty acid profile and oil yield in six different varieties of fresh an dry samples of coconuts (*Cocos nucifera*), 2006, Pakistan Journal of Nutrition, 5(2), pp. 106-109.*
Bezard. J. et al., Triglyceride compositoin of coconut oil, 1971, Anaimale et de la Nutrition, Facutlife des Science, 21, pp. 134-139.*
Bondioli, P., et al., Squalene recovery from olive oil deodorizer distillates, 1993, JAOCS, vol. 70, No. 8, pp. 763-766.*
Connor, W., alpha-linolenic acide in health and disease, 1999, Am. J. Clin. Nutr., 69, pp. 82-828.*
"International Cosmetic Ingredient Dictionary and Handbook Eleventh Edition," 2006, The Cosmetic, Toiletry and Fragrance Association, XP002538967, p. 840.
"International Cosmetic Ingredient Dictionary and Handbook Eleventh Edition," 2006, The Cosmetic, Toiletry and Fragrance Association, XP002540692, pp. 834-835.

* cited by examiner

*Primary Examiner* — Yate K Cutliff
(74) *Attorney, Agent, or Firm* — Rothwell, Figg, Ernst & Manbeck P.C.

(57) ABSTRACT

Mixture comprising esters of saturated $C_{16}$-$C_{18}$ fatty acid and unsaturated $C_{16}$-$C_{18}$ fatty acids with 2-ethyl-hexyl alcohol, said esters being in an amount ranging from 90% to 100% by weight with respect to the total weight of the mixture. The cosmetic compositions containing such a mixture formulated in topical form have a moisturizing, emollient, elasticizing and skin compactness and smoothness improving action.

15 Claims, No Drawings

MIXTURE OF FATTY ACID ESTERS OF NATURAL ORIGIN AND ITS USE IN COSMETIC PREPARATIONS BASED ON OLIVE OIL DERIVATIVES

CROSS-REFERENCE TO RELATED APPLICATIONS

The present application is a national stage filing under 35 U.S.C. §371 of PCT/IB2009/054542, filed on 15 Oct. 2009, and claims the benefit of priority to Italian Application MI2008A001884, filed 24 Oct. 2008, each application is incorporated herein by reference in its entirety.

The present invention concerns a mixture comprising esters of saturated and unsaturated aliphatic carboxylic acids with monohydroxy alcohols, as well as the process for obtaining them and their use in cosmetic preparations based on active ingredients derived from natural products. In particular, such a mixture comprises the aforementioned esters derived from saturated and unsaturated fatty acids with medium-long chain and it is used to produce preparations in the form of emulsions.

Such esters are per se already known and used to produce, for example, biofuels or emulsions used in moulds for manufacturing cement products. However, such esters have proven to have useful properties in totally different fields from those known up to now. Indeed, in the form of a mixture thereof, with other components also being present, they have applications in the field of production of preparations for treating the body, and not exclusively the human body. In particular, there are preparations for topical use, with uses both in the fields of pharmaceuticals and cosmetics.

The mixture of the present invention, which is of natural origin since it is obtained from olive oil (fruit of the *Olea Eureopaea*), as well as being non-irritant and hypoallergenic, performs various dermatological actions, mainly emollient, moisturising, elasticising, and/or skin compactness and/or smoothness improving actions.

STATE OF THE ART

Preparations of exclusively natural origin that possess the same dermatological actions as the mixture of the present invention are known. An example is the unsaponifiable component of olive oil. Such a component comprises a high percentage of saturated and unsaturated hydrocarbon compounds, including one of the main ones which is squalene, a molecule with high molecular weight with six double bonds.

In cosmetic preparations, said unsaponifiable component is used not only for its dermatological action as an emollient, moisturiser and elasticiser, but also as stabiliser of preparations obtained with it. However, when such an unsaponifiable component is present in significant amounts (i.e. at least around 3%-5% by weight), its use entails various problems in the final preparation, linked mainly to the squalene due both to its chemical structure and to some of its chemical-physical characteristics. For example, the high degree of desaturation of squalene, due to six double bonds, makes it easily subject to oxidation, and therefore to degradation of the molecule. The consequence is an alteration of the functionality and also of the organoleptic characteristics of the final preparations, such as low stability over time, with consequent separation of the aqueous phase after a short period of time.

Said unsaponifiable component also displays an organoleptic profile that is not ideal for application in the field of cosmetics. The biggest drawback concerns the releasing of a strong and characteristic smell. It is difficult to mask such a smell in the final preparations, to the point that it is noticeable even when there is specially added perfume.

Moreover, another drawback is given by its intense colour, which is deep yellow. This intense colour can create difficulties in obtaining preparations with a very light colour.

Lastly, visually, said unsaponifiable component looks cloudy and also dishomogeneous due to the presence of material in suspension.

Therefore, in the case of application in the cosmetic field there is a desire to have compounds that are as colourless, odourless and clear as possible.

With regard to the industrial production of said unsaponifiable component, notable difficulties are encountered. These are due, on the one hand, to the difficulty in reproducing its chemical-physical characteristics in a constant manner, making them significantly different from one batch produced to the other. On the other hand, due to the current production methods of olive oil, the isolation of its unsaponifiable component is made more difficult and the quality of the product obtained also decreases. Both of these problems thus involve increased production costs.

Therefore, there is a need to have a compound that is equipped with dermatological properties that give effects that are very similar to that of the unsaponifiable component and that, moreover, does not have the aforementioned drawbacks. Moreover, there is a need to have active ingredients that, once introduced in the final preparations, give a feeling of coolness on the skin, instead of a feeling of heat, as occurs with preparations containing said unsaponifiable component as the only active ingredient.

DESCRIPTION OF THE INVENTION

It has now been surprisingly found that all of the aforementioned drawbacks are overcome by using a mixture of esters of 2-ethyl-1-hexyl alcohol with saturated $C_{16}$-$C_{18}$ and unsaturated $C_{16}$-$C_{18}$ fatty acids. Such fatty acids in the form of their derivatives are already present in olive oil and are obtained in free form directly from the oil.

The mixture of the present invention has a good balance between chemical-physical properties, organoleptic properties and dermatological properties. Such properties are of a similar order of magnitude to, and in certain cases even better than, that of just the unsaponifiable component.

The mixture of the present invention, unlike the unsaponifiable component, as a whole has a chemical nature much closer to that of human sebum and this offers some advantages. On the one hand, such a chemical nature ensures that it is able to be more easily absorbed by the skin and also penetrate deeper, without blocking the skin's pores. Moreover, cosmetic preparations that contain it make the skin softer and smoother, thus also demonstrating its emollient properties. On the other hand, it is less of an irritant, and in particular it causes less oedema and erythema reaction. Indeed, the values of the average irritation index are substantially lower, which means that the preparations obtained with the mixture of the present invention are much better tolerated.

The mixture of the present invention has a chemical composition that gives greater stability to the final preparation. The stability of the latter is due both to a lower degradation of most of the molecules that form the active ingredient or over longer periods of time, and to greater stability of the formulation, since, indeed, there is no separation of the aqueous phase.

In terms of the olfactory sensation, the aforementioned mixture has a slight or imperceptible smell, whereas from the visual point of view, it has the appearance of a homogeneous, clear and limpid liquid, even at low temperatures, having a clouding point of less than or equal to −15° C. Such characteristics also have a positive influence upon the final preparation that also has a homogeneous appearance.

In terms of texture, during and after application on the skin, the cosmetic preparations, both as water in oil emulsions and oil in water emulsions, containing the mixture of the present invention, have a silky and pleasant-feeling texture.

A further advantage is represented by the fact that it has a very low freezing temperature, and therefore even in relatively harsh temperature conditions there are no mutations of the phase that cause alterations in appearance, of the preparation and of the applicability of the final preparation.

Another advantage of the mixture of the present invention consists of the fact that it can be obtained through a production process that gives a product with constant and reproducible chemical-physical characteristics, as well as being easy to carry out.

Therefore, the object of the present invention is a mixture comprising saturated $C_{16}$-$C_{18}$ fatty acid esters and unsaturated $C_{16}$-$C_{18}$ fatty acid esters with 2-ethyl-1-hexyl alcohol, such esters being in an overall amount of between 90.0% and 100.0%, preferably from 97.0% to 99.9%, more preferably between 98.5% and 99.9%, by weight with respect to the total weight of the mixture.

In the present description all the indicated ranges must be taken to include the extreme values.

Since the starting mixture of fatty acids is directly derived from olive oil, and thus of natural origin, its composition is variable according to the type and batch of olive oil used; amongst the fatty acids present in the mixture (and therefore in glyceride form in the olive oil) the main ones are stearic, oleic, linoleic and palmitic acids and in particular oleic acid is the one present in the greatest percentage.

More specifically, the mixture of esters object of the present invention indicatively contains the following amounts of esters:

from 550% to 83.0%, preferably from 60.0% to 75.0% by weight of ester of oleic acid,
from 3.5% to 21.0%, preferably from 5.0% to 12.0% by weight of the ester of linoleic acid,
from 7.5% to 20.0%, preferably from 13.0% to 17.0%, by weight of the ester of palmitic acid,
from 0.5 to 5.0%, preferably from 3.0% to 5.0%, by weight of the ester of stearic acid, and
from 0.3% to 3.5%, preferably from 1.0% to 3.0% by weight of the ester of palmitoleic acid.

In addition to the aforementioned esters, esters of other fatty acids with medium-long chain and long chain may be present in such a mixture; more specifically, they are esters of 2-ethyl-1-hexyl alcohol with polyunsaturated $C_{18:3}$ fatty acids and $C_{20}$-$C_{24}$ fatty acids, both saturated and unsaturated. Such esters are in a variable amount, indicatively between 0.1% and 1.5% with respect to the mixture; typical examples of such acids are esters of linolenic, arachidic, eicosenoic, behenic and lignoceric acids.

In addition to the aforementioned esters, the mixture also contains an unsaponifiable component of olive oil (present in the olive oil used as raw material) in an amount generally between 0.2% and 2.0%, preferably between 0.5% and 1.5%, by weight with respect to the weight of the mixture. Such an unsaponifiable component has the same chemical composition as the unsaponifiable component of olive oil of *Olea Europaea*, from which it derives.

According to one of the preferred aspects of the present invention, the mixture of the present invention consists of (a) saturated $C_{16}$-$C_{18}$ fatty acid esters and unsaturated $C_{16}$-$C_{18}$ fatty acid esters with 2-ethyl-1-hexyl alcohol in an amount of between 97.0% and 99.9% by weight, preferably between 98.5% and 99.9%; (b) esters of 2-ethyl-1-hexyl alcohol with polyunsaturated $C_{18:3}$ fatty acids and $C_{20}$-$C_{24}$ fatty acids, both saturated and unsaturated, in an amount of between 0.1% and 1.5% by weight; (c) the unsaponifiable component of olive oil in an amount of between 0.2% and 2.0% by weight, preferably between 0.5% and 1.5% (where said percentages should always be taken with respect to the weight of the mixture), the possible remainder up to 100% essentially consisting of impurities, like for example 2-ethyl-1-hexyl alcohol.

The mixture of the present invention typically has a saponification value (or number) of between 120 and 170, preferably between 135 and 155 $mg_{KOH}/g$. Moreover, its iodine value (or number) typically varies between 40 and 80, preferably between 50 and 70 $gI_2/100$ g. The acidity value (or number) of the mixture typically varies between 1 and 5, preferably between 2 and 3 $mg_{KOH}/g$. Such values are measured according to the methods described later on.

A preferred method for preparing the mixture of the present invention consists of using olive oil as the starting product.

In particular, the process comprises the following stages:
 a) saponification of the glyceride esters of olive oil and then separation of the mixture comprising fatty acids and the unsaponifiable component; and
 b) esterification reaction with 2-ethyl-1-hexyl alcohol of the mixture obtained in the previous stage a).

The reactions of the aforementioned stages a) and b) take place using methods and conditions well known to the man skilled in the art.

Indicatively:
 stage (a) comprises the saponification of the esters of olive oil that takes place using strong bases and operating at a hot temperature. Alkaline or alkaline-terrous metals are generally used as strong bases, preferably sodium hydroxide or potassium hydroxide. Such bases are generally used in the form of an aqueous solution with a typical normality of around 5. The reaction takes place at a temperature generally between 80° C. and 120° C. for at least 1 hour. The molar ratio between esters to be hydrolysed and the strong base is at least 3 to 1, preferably between 3.1 to 1 and 3.5 to 1. At the end it is acidified with a strong acid (e.g. HCl), for example in aqueous solution with a normality of between 1 and 5; and finally the organic phase is separated; and
 stage (b) comprises the esterification of the free fatty acids obtained in stage (a) with 2-ethyl-1-hexyl alcohol that occurs at temperatures of between 100° C. and 140° C. for at least 2 hours, using acidic catalysts such as sulphuric acid and p-toluenesulfonic acid indicatively in an amount of between 0.1% and 1.0%, preferably between 0.3% and 0.5%, by weight with respect to the product to be esterified; the molar ratio between free fatty acids to be esterified and alcohol is indicatively at least 1 to 1, preferably between 1 to 1 and 1 to 1.5.

Hereafter the analytical methods with which the mixture of the present invention has been characterised are described hereafter:
 gas-chromatography analysis: a Gas chromatograph Carlo Erba HRGC-MEGA 2 with FID detector is used, equipped with capillary analysis column STABILWAX-DA (specification for the analysis of fatty acid esters) 30 meters long, with internal diameter of 0.32 mm and with thickness of the stationary phase of 0.25 micron; the analysis is carried out in programmed temperature conditions from 160° C. to 230° C. with an increase of 10° C. per minute and with an injection temperature of 230° C. and FID temperature of 250° C.

Acidity value (or number): using the method 01/2008:20501 by EUROPEAN PHARMACOPEIA 6.0.

Saponification value (or number): using the method 01/2008:20506 by EUROPEAN PHARMACOPEIA 6.0.

Iodine value (or number): using the method 01/2008:20504 by EUROPEAN PHARMACOPEIA 6.0.

A further finding of the present invention concerns cosmetic preparations comprising the aforementioned mixture comprising the fraction including a mixture of esters of saturated $C_{16}$-$C_{18}$ fatty acids and unsaturated $C_{16}$-$C_{18}$ fatty acids with 2-ethyl-1-hexyl alcohol.

In such preparations the mixture is in an amount of between 1% and 15% by weight, preferably between 2% and 10% by weight.

The aforementioned cosmetic preparations are of various types such as oils, detergents in general (hair, body, intimate parts), make-up products, sun-protection products; preferably they are emulsions and more specifically they are of the oil in water type (O/W), the water in oil type (W/O), or of the siliconic type (W/S). O/W and W/O emulsions are the preferred ones.

The preparations of the present invention are for topical use and are preferably in the form of creams.

The aforementioned topical preparations also comprise further components, which are the ones typically used in dermatology. Examples of such components are: emulsifiers, rheological modifiers, active ingredients, perfumes, dyes, preservatives, etc.

The preparations of the present invention are prepared according to the mixing methods known in the field. Typically this is done through mixing/homogenisation at temperatures of between 20° C. and 90° C., using mechanical agitation systems or through turbo emulsifiers/homogenisers or both of the aforementioned systems.

The following examples are provided for purely illustrative purposes and do not limit the present invention.

Tests have been carried out on the mixtures and preparations of the present invention to evaluate the characteristics and properties thereof. Hereafter the methodology with which such tests were carried out is described.

Instantaneous stability test: carried out, 24 hours after the preparation of the sample, through high-speed centrifuging (centrifuge at 5000 revolutions for 60 minutes Ageing stability tests: the sample is visually examined to evaluate its stability over time and in different storage temperature conditions, such as:

3 months at 5° C.-6 months at room temperature (both in the light and in the dark)

3 months at 40° C.-1 month at 50° C.

Irritant power (epicutaneous Patch Test under occlusion): evaluated after applications under occlusion through a Finn Chamber® device. The active ingredient or the cosmetic preparation are applied on the skin of the back of a predetermined (statistically significant) number of healthy adult volunteers of both sexes; the total application time is 48 hours. They are checked for signs of erythema and oedema at predetermined times.

Sensitizing power (HYPOALLERGENICITY): evaluated through repeated Patch Tests and it is divided into 2 steps:

a) Induction patch test: the active ingredient or the cosmetic preparation is applied onto the skin of the back of a predetermined (statistically significant) number of healthy adult volunteers of both sexes; the application of the product on the skin lasts 24 hours and the clinical testing is carried out 24 hours after removal of the adhesive strip detecting the possible presence of signs of erythema and oedema; the applications are repeated 9 times on the same skin area.

b) Patch test for detecting sensitization: 15 days after the end of step a), a single patch test is repeated lasting 48 hours in a different skin area from the previous one; the skin reactions are evaluated 24, 48 and 72 hours after the removal of the adhesive strip, detecting the possible presence of signs of erythema and oedema Hydration index: evaluated using the following two different methods:

Method A)—Short Term Hydration:

the active ingredient or the cosmetic preparation is applied on the skin of the forearm of a predetermined (statistically significant) number of healthy adult volunteers of both sexes. The degree of hydration is evaluated at predetermined times (preferably after 30 minutes and after 2 hours), with the Corneometer®

Method B):—Long Term Hydration:

the cosmetic preparation is applied on the skin of one side of the face of a predetermined (statistically significant) number of healthy adult volunteers of both sexes; the other side of the face is normally applied, at the same time and using the same methods, with a reference cosmetic product (placebo) prepared with an identical formula apart from the active ingredient whose moisturising capability it is wished to measure. The application is carried out twice per day (morning and evening) with gentle massaging. The results are collected on the 15th and 30th day after the start of the treatment, with a Corneometer®

Transepidermal water loss (TEWL): method B) described above is used, carrying out the measurements with a Tewameter®.

Skin elasticity: method B) described above is used, carrying out the measurements with a Cutometer®.

Skin compactness and smoothness: method B) described above is used; the measurement of the results obtained is not with instruments but is evaluated from the clinical point of view directly by a dermatologist, by assigning a score that can vary from 1 to 4.

EXAMPLES

Example 1

Preparation of the Mixture Comprising the Fraction Including the Mixture of Fatty Acid Esters 500 g of olive oil of *Olea Europaea* and 86 g of sodium hydroxide are placed in a 2 liter flask, dissolved in 800 ml of water; it is agitated for 2 hours at a temperature of 95° C. At the end of the reaction it is acidified with hydrochloric acid 2N and it is left to agitate slowly for 30 minutes. The two phases are separated, recovering 460 g of organic phase, consisting of the fatty acids and the unsaponifiable component of the olive oil.

The fatty acids thus produced placed under agitation in a 1 liter flask, are added to with 256 g of 2-ethyl-1-hexanol and 3.5 g of p-toluenesulfonic acid. The mixture is reacted for a time of 3 hours at a temperature of 120° C. At the end it is cooled to 50° C., and the product is washed with 200 ml of water and the excess alcohol is distilled up to 100° C. About 590 g of the mixture of fatty acid esters is recovered in the form of yellow-coloured liquid product.

Gas-chromatography analysis discloses the qualitative composition illustrated in table 1.

TABLE 1

| Type of acylic radical of ester | Amount of ester in the mixture (% by weight) |
|---|---|
| Stearyl | 3.1 |
| Oleiyl | 66.4 |
| Linoleyl | 10.1 |
| Palmityl | 15.8 |
| Palmitoiyl | 1.1 |
| Others (linolenyl + arachidyl + beenyl + lignoceryl) | 1.3 |
| Unsaponifiable component from olive oil (squalene) | 1.2 |

The chemical-physical characteristics of the mixture obtained in example 1 are shown, in comparison with those of the unsaponifiable component of the olive oil used in the comparative examples, in the following table 2.

TABLE 2

| Chemical-physical characteristics | MIXTURE of example 1 | UNSAPONIFIABLE COMPONENT |
|---|---|---|
| Physical state | Limpid liquid | Very turbid liquid with material in suspension |
| Colour (visual) | Light yellow | Deep yellow |
| Colour (GARDNER[2] scale) | 5 max. | Not measurable (due to the material in suspension) |
| Smell | Light, characteristic | Strong, characteristic |
| Active substances (%) | 99.0 | 97.0 |
| Acidity value ($mg_{KOH}$/g) | Max. 3 | Max. 3 |
| Saponification value ($mg_{KOH}$/g) | 130-160 | Max. 10 |
| Iodine value ($gI_2$/100 g) | 50-70 | 270-370 |

[2] evaluation of the colour by comparison with reference colours scale (which ranges from 1 to 18).

Example 2 and Comparative Example 1

Preparation of a Cosmetic Preparation of the Water in Oil Emulsion Type

Steps A and B are prepared separately, by mixing together the various components, under light agitation and heating up to a temperature of around 80° C.; phase B is then added to phase A (maintaining the same temperature) under vigorous agitation, preferably using high speed homogenisation systems with apparatuses like turboemulsifiers such as SILVERSON or TURRAX, for about 10 minutes. The preparation obtained is then cooled with a water bath, under light agitation; at temperatures below 40° C. phase C (preservative system) is then added.

Two cosmetic preparations are prepared, according to the described procedure, with the components and the relative amounts shown in table 3, for example 2 using the mixture of esters obtained in example 1 and for the comparative example 1 using the unsaponifiable component of the olive oil (squalene).

Table 3 also shown the result of the instantaneous stability tests and of the ageing stability tests. Table 4 also shows the sensorial properties of the cosmetic preparations thus obtained.

TABLE 3

| Component | EXAMPLE 2 (% by weight) | COMPARATIVE EXAMPLE 1 (% by weight) |
|---|---|---|
| Phase A | | |
| Mixture of esters | 10 | 0 |
| Unsaponifiable component | 0 | 10 |
| Sorbitan Olivate[1] | 7.5 | 7.5 |
| Cyclomethicone | 10 | 10 |
| Neopentanoate isodecyl | 5.0 | 5.0 |
| Phase B | | |
| Demineralised water | 62.7 | 62.7 |
| Glycerine | 3.0 | 3.0 |
| $MgSO_4$ | 1.0 | 1.0 |
| Phase C | | |
| Preservative system[2] | 0.8 | 0.8 |
| Stability of the preparation | | |
| Instantaneous stability | No separation of phases | Slight separation of oil phase |
| Ageing stability (at 40° C. for three months) | No separation of phases | Separation of the aqueous phase with formation of water droplets |

[1] This is a cosmetic emulsifier of natural origin, already produced and commercialised by B&T
[2] This is a commercial product with antimicrobial and antimycotic properties, normally used in cosmetic preparations. It is to prevent contamination both from bacteria and from mould

TABLE 4

| Property | EXAMPLE 2 | COMPARATIVE EXAMPLE 1 |
|---|---|---|
| Visual appearance | White Opaque Smooth Pearly | white-yellow opaque smooth glossy |
| Smell | Imperceptible | strong |
| Texture | Light homogeneous Silky Soft | consistent homogeneous velvety soft |
| Application on the skin | ease of application silky sensation sensation of heat | ease of application velvety sensation sensation of heat |

Example 3 and Comparative Example 2

Preparation of a Cosmetic Preparation of the Oil in Water Emulsion Type

Phases A and B are prepared separately, mixing together the various components, under agitation and heating up to a temperature of around 80° C.; phase A is then added to phase B (keeping the same temperature) under vigorous agitation, preferably using high speed homogenisation systems with apparatuses like turboemulsifiers such as SILVERSON or TURRAX, for about 10 minutes. The preparation obtained is then cooled with a water bath, agitating gently; at temperatures below 40° C. phase C (preservative system and perfume) is then added.

Two cosmetic preparations are prepared, according to the described procedure, with the components and the relative amounts shown in table 5, using the mixture of esters obtained in example 1 for example 3 and using the unsaponifiable component of olive oil (squalene) for the comparative example 2; in parallel a placebo (reference product prepared with an identical formula minus the active ingredients under examination) is prepared just with the base components of the preparation.

Table 6 shows the sensorial properties of the final preparations thus obtained.

TABLE 5

| Component | EXAMPLE 3 (% by weight) | COMPARATIVE EXAMPLE 2 (% by weight) | Placebo (% by weight) |
|---|---|---|---|
| Phase A | | | |
| Mixture of esters | 5.0 | 0 | 0 |
| Unsaponifiable component | 0 | 5.0 | 0 |
| Cetearyl alcohol | 2.0 | 2.0 | 2.0 |
| Ceteareth-20 | 1.0 | 1.0 | 1.0 |
| Phase B | | | |
| Demineralised water | 90.75 | 90.75 | 95.75 |
| Sodium polyacrylate | 0.65 | 0.65 | 0.65 |
| Phase C | | | |
| Preservative system | 0.4 | 0.4 | 0.4 |
| Perfume | 0.2 | 0.2 | 0.2 |

TABLE 6

| Property | EXAMPLE 3 | COMPARATIVE EXAMPLE 2 |
|---|---|---|
| Visual appearance | white opaque smooth very shiny homogeneous light | dirty white opaque smooth shiny homogeneous heavy |
| Smell | light | strong |
| Consistency | fluid smooth homogeneous | creamy cushion effect homogeneous |
| Application on the skin | ease of application Cool sensation Great sensation of smoothness Strong silky sensation | ease of application Hot sensation Sensation of smoothness Silky sensation |

Instrument-based Tests and Clinical Evaluations

A) Tests Carried Out Directly on the Mixture of Esters of Example 1 and on the Unsaponifiable Component of Olive Oil (Squalene):

in order to investigate the irritant power of the preparations percutaneous tests are carried out with adhesive plasters at the ends of which it is evaluated whether and to what extent skin phenomena like erythema and oedema reaction have occurred from which the values of the average irritation indices (AII) are calculated: index values equal to or less than 0.5 indicate that there is no irritation.

The following tables 7 and 8 show such values from which it can be seen that the erythema type irritant power of the mixture of esters object of the present invention is more than halved with respect to that of the unsaponifiable component of olive oil (squalene).

TABLE 7

| | Erythema | |
|---|---|---|
| Time | MIXTURE of example 1 | UNSAPONIFIABLE COMPONENT |
| 15 minutes | 0.12 | 0.28 |
| 1 hour | 0.04 | 0.12 |
| 24 hours | 0.00 | 0.00 |

TABLE 8

| | Oedema | |
|---|---|---|
| Time | MIXTURE of example 1 | UNSAPONIFIABLE COMPONENT |
| 15 minutes | 0.00 | 0.00 |
| 1 hour | 0.00 | 0.00 |
| 24 hours | 0.00 | 0.00 |

Relative to sensitizing power (HYPOALLERGENICITY) both the mixture of esters object of the present invention and the unsaponifiable component of olive oil are not sensitizing and therefore both are not considered to be hypoallergenic products.

B) Tests Carried Out on the Cosmetic Preparations Containing the Mixture of Esters of Example 1 (Example 3) and the Unsaponifiable Component of Olive Oil (Squalene) (Comparative Example 2):

Using the aforementioned method (A), the hydration index of the mixture of the present invention (with 5% content in the cosmetic preparation shown in Example 3), is higher than that of the unsaponifiable component (contained in the same concentration in the cosmetic preparation shown in comparative Example 2) when evaluated over a short time period.

The following table 9 shows the hydration results, expressed in corneometer units (u.c.) and the percentage hydration increase with respect to time zero in comparison with skin area that has not been treated (control).

TABLE 9

| | Hydration index | | | | | |
|---|---|---|---|---|---|---|
| | MIXTURE of example 1 | | UNSAPONIFIABLE COMPONENT | | Control | |
| Time (minutes) | u.c. (Average value) | Increase % | u.c. (Average value) | Increase % | u.c. (Average value) | Increase % |
| 0 | 60.4 | — | 57.2 | — | 56.5 | — |
| 30 | 71.0 | +17.5 | 67.3 | +17.6 | 57 | +0.9 |
| 120 | 71.6 | +18.5 | 62.4 | +9.1 | 56.8 | +0.6 |

Using the aforementioned method (B), from the data given in the following tables 10 and 11 it can be seen that the hydration index between the mixture of the present invention and the unsaponifiable component have values of the same order of magnitude, particularly 30 days after the start of the treatment.

TABLE 10 hydration index

| Time (days) | MIXTURE of the example 1 | | Placebo | |
|---|---|---|---|---|
| | u.c. (Average value) | Increase % | u.c. (Average value) | Increase % |
| 0 | 55.2 | — | 53.9 | — |
| 15 | 59.5 | 7.9 | 55.3 | 2.5 |
| 30 | 62.5 | 13.3 | 54.9 | 1.8 |

TABLE 11 hydration index

| Time (days) | UNSAPONIFIABLE COMPONENT | | Placebo | |
|---|---|---|---|---|
| | u.c. (Average value) | Increase % | u.c. (Average value) | Increase % |
| 0 | 57.2 | — | 56.6 | — |
| 15 | 62.7 | 9.7 | 58.2 | 2.9 |
| 30 | 64.2 | 12.3 | 57.8 | 2.1 |

Transepidermal Water Loss (TEWL)

The following two tables show the transepidermal water loss values of the skin treated with the mixture of the present invention, compared with those of the unsaponifiable component and of the placebo.

The comparison shows that the mixture of the present invention reduces the water loss by the same amount as the unsaponifiable component on the 15th day, but the reduction is substantially greater on the 30th day after the start of the treatment.

TABLE 12

Transepidermal water loss

| Time (days) | MIXTURE of the example 1 | | Placebo | |
|---|---|---|---|---|
| | Average value (g/h/m$^2$) | % | Average value (g/h/m$^2$) | % |
| 0 | 14.1 | — | 13.3 | — |
| 15 | 10.2 | −27.4 | 11.6 | −12.9 |
| 30 | 9.4 | −33.2 | 11.5 | −13.2 |

TABLE 13

Transepidermal water loss

| Time (days) | UNSAPONIFIABLE COMPONENT | | Placebo | |
|---|---|---|---|---|
| | Average value (g/h/m$^2$) | % | Average value (g/h/m$^2$) | % |
| 0 | 14.1 | — | 11.8 | — |
| 15 | 10.2 | −27.5 | 10.7 | −9.7 |
| 30 | 10.1 | −28.2 | 10.6 | −10.4 |

Skin Elasticity

The following two tables show the elasticity values of the skin treated with the mixture of the present invention, compared with those of the unsaponifiable component and of the placebo. The comparison shows that the mixture and the unsaponifiable component produce an elasticising effect, 30 after the start of the treatment, of the same order of magnitude.

TABLE 14 skin elasticity

| Time (days) | MIXTURE of the example 1 | | Placebo | |
|---|---|---|---|---|
| | Average value | % | Average value | % |
| 0 | 0.7356 | — | 0.7608 | — |
| 15 | 0.7839 | 6.6 | 0.7666 | 0.8 |
| 30 | 0.8077 | 9.8 | 0.7715 | 1.4 |

TABLE 15 skin elasticity

| Time (days) | UNSAPONIFIABLE COMPONENT | | Placebo | |
|---|---|---|---|---|
| | Average value | % | Average value | % |
| 0 | 0.7577 | — | 0.7820 | — |
| 15 | 0.8051 | 6.3 | 0.7911 | 1.2 |
| 30 | 0.8143 | 7.5 | 0.7998 | 2.3 |

In Vivo Clinical Evaluations

Skin Compactness and Smoothness

The following four tables show the compactness (Tables 16 and 17) and the smoothness values (Tables 18 and 19) found in the skin treated with the mixture of the present invention and the unsaponifiable component, compared with those of the placebo.

The comparison shows that both skin compactness and smoothness brought about by the mixture of the present invention are substantially greater 30 days after the start of the treatment with respect to the compactness and smoothness brought about by unsaponifiable component of olive oil (squalene).

TABLE 16 skin compactness

| Time (days) | MIXTURE of the example 1 | | Placebo | |
|---|---|---|---|---|
| | Average value | % | Average value | % |
| 0 | 1.9 | — | 1.9 | — |
| 15 | 2.1 | 10.5 | 2.1 | 10.5 |
| 30 | 2.4 | 26.3 | 2.1 | 10.5 |

TABLE 17 skin compactness

| Time (days) | UNSAPONIFIABLE COMPONENT | | Placebo | |
|---|---|---|---|---|
| | Average value | % | Average value | % |
| 0 | 2.1 | — | 2.1 | — |
| 15 | 2.2 | 4.8 | 2.2 | 4.8 |
| 30 | 2.4 | 14.3 | 2.3 | 9.5 |

TABLE 18

| | skin smoothness | | | |
|---|---|---|---|---|
| Time | MIXTURE of the example 1 | | Placebo | |
| (days) | Average value | % | Average value | % |
| 0 | 1.8 | — | 1.8 | — |
| 15 | 1.9 | 5.5 | 1.8 | 0 |
| 30 | 2.3 | 27.8 | 1.9 | 5.5 |

TABLE 19

| | skin smoothness | | | |
|---|---|---|---|---|
| Time | UNSAPONIFIABLE COMPONENT | | Placebo | |
| (days) | Average value | % | Average value | % |
| 0 | 2.1 | — | 2.1 | — |
| 15 | 2.2 | 4.8 | 2.1 | 0 |
| 30 | 2.5 | 19.0 | 2.2 | 4.8 |

The invention claimed is:

1. A mixture comprising esters of saturated $C_{16}$-$C_{18}$ fatty acids and unsaturated $C_{16}$-$C_{18}$ fatty acids with 2-ethyl-hexyl alcohol and an unsaponifiable component, said esters being in an amount ranging from 90% to 100% by weight with respect to the total weight of the mixture and said unsaponifiable component being in an amount ranging from 0.2% to 2.0% by weight with respect to the total weight of the mixture.

2. The mixture according to claim 1 wherein said esters are in an amount ranging from 97.0% to 99.9% by weight with respect to the total weight of the mixture.

3. The mixture according to claim 1 wherein said saturated $C_{16}$-$C_{18}$ fatty acids and unsaturated $C_{16}$-$C_{18}$ fatty acids are oleic acid, linoleic acid, palmitic acid and stearic acid.

4. The mixture according to claim 1 wherein the aforementioned mixture of esters consists of 55.0 to 83.0% by weight of oleic acid ester, 3.5 to 21% by weight of linoleic acid ester, 7.5 to 20.0% by weight of palmitic acid ester and 0.5 to 5.0% by weight of stearic acid ester.

5. The mixture according to claim 4 wherein the aforementioned mixture of esters consists of 60.0 to 75.0% by weight of oleic acid ester, 5.0 to 12.0% by weight of linoleic acid ester, 13.0 to 17.0% by weight of palmitic acid ester and 3.0 to 5.0% by weight of stearic acid ester.

6. The mixture according to claim 1, characterised in that it also comprises esters of 2-ethyl-1-hexyl alcohol with polyunsaturated $C_{18:3}$ fatty acids and $C_{20}$-$C_{24}$ fatty acids, both saturated and unsaturated, such esters being in an amount of between 0.1% and 1.5% by weight with respect to the total weight of such a mixture.

7. Process for preparing the mixture according to claim 1, comprising the following stages:

stage (a): comprising saponification of the esters of olive oil that takes place using strong bases and operating at a high temperature, subsequent acidification with a strong acid and separation of the organic phase; and stage (b): comprising esterification of free fatty acids obtained in stage (a) with 2-ethyl-1-hexyl alcohol.

8. A cosmetic preparation comprising the mixture according to claim 1 in an amount varying from 1 to 15% by weight with respect to the weight of the total preparation.

9. The preparation of claim 8 wherein the mixture is in an amount of between 2 and 10% by weight with respect to the weight of the total preparation.

10. The preparation according to claim 8 formulated in cream form.

11. The preparation of claim 10 formulated in the form of an oil in water emulsion or a water in oil emulsion.

12. A method of stabilizing a cosmetic preparation comprising adding a stabilizing amount of the mixture of claim 1 to the cosmetic preparation, wherein the amount of said mixture is from 1 to 15% by weight with respect to the weight of the total preparation.

13. A method of maintaining skin's hydration and/or elasticity comprising topically applying the preparation of claim 8 to skin.

14. The mixture according to claim 1, wherein said esters are in an amount ranging from 98.5% to 99.9% by weight with respect to the total weight of the mixture.

15. A method of improving skin compactness and/or skin smoothness comprising topically applying the preparation of claim 8 to skin.

* * * * *